United States Patent [19]

Willis et al.

[11] 4,197,089
[45] Apr. 8, 1980

[54] REDUCING GAS SENSOR

[75] Inventors: Alexander N. Willis, Los Altos; Margers Silarajs, San Jose, both of Calif.

[73] Assignee: Ambac Industries, Incorporated, New York, N.Y.

[21] Appl. No.: 870,600

[22] Filed: Jan. 18, 1978

Related U.S. Application Data

[63] Continuation-in-part of Ser. No. 741,359, Nov. 12, 1976, abandoned, which is a continuation of Ser. No. 643,521, Dec. 22, 1975, abandoned.

[51] Int. Cl.² .................... G01N 27/16; G01N 33/00
[52] U.S. Cl. ........................... 23/232 E; 324/71 SN; 340/633; 340/634; 422/96; 422/97; 422/98
[58] Field of Search ................... 23/254 E, 232 E; 324/71 SN; 338/34; 340/237 R, 633, 634; 73/27; 422/94-98

[56] References Cited

U.S. PATENT DOCUMENTS

| 3,479,257 | 11/1969 | Shaver ............................ 23/232 E X |
| 3,549,329 | 12/1970 | Silverman et al. ................ 23/254 E |
| 3,695,848 | 10/1972 | Taguchi ............................ 23/254 E |
| 3,820,958 | 6/1974 | Cheng et al. ....................... 23/254 E |
| 3,865,550 | 2/1975 | Bott et al. .......................... 23/232 E |
| 3,901,067 | 8/1975 | Boardman, Jr. et al. ...... 23/254 E X |
| 3,961,248 | 6/1976 | Kawamura ..................... 23/254 E X |
| 3,999,997 | 12/1976 | Milarn ............................. 23/254 E |
| 4,039,941 | 8/1977 | Morrison ...................... 23/254 E X |

Primary Examiner—Michael S. Marcus

[57] ABSTRACT

A sensor for the quantitative determination of reduction of a gas in which a thin tungsten oxide film detector element includes means for providing a specificity for the gas to be detected with respect to other gases. If ammonia is to be detected, a platinum catalyst is utilized. If hydrogen sulfide is to be detected, tungsten trioxide is used in the film.

6 Claims, 5 Drawing Figures

REDUCING GAS SENSOR

CROSS-REFERENCE TO RELATED APPLICATION

This application is a continuation-in-part of our co-pending U.S. patent application Ser. No. 741,359 filed Nov. 12, 1976, now abandoned which application was a continuation of our U.S. application Ser. No. 643,521, filed Dec. 22, 1975, now abandoned.

BACKGROUND OF THE INVENTION

1. Field of the Invention

This invention relates to metallic oxide detectors for reducing gases.

2. Description of the Prior Art

The use of a thin film of metallic oxide, such as tungsten oxide, whose surface has been activated by the deposition of a platinum catalyst, to make a quantitative analysis of hydrogen or other reducing gases is described in U.S. Pat. No. 3,479,257, issued Nov. 18, 1969, to Paul J. Shaver. As distinguished from conventional catalytic combustion sensors, such as the sensor element described in U.S. Pat. No. 3,586,486, issued June 22, 1971 which utilize a change in element resistance due to a change in temperature to provide the concentration indication, the sensor in U.S. Pat. No. 3,479,257 initiates a chemical reduction reaction which changes the carrier density in the oxide film as a function of the gas reduced, thereby producing a change in film resistance to provide the concentration indication.

The sensors described in U.S. Pat. No. 3,479,257 may be utilized for the quantitative analysis of various gases such as hydrogen, hydrogen sulfide, and anhydrous ammonia, and hydrazine, propane, butane, methyl alcohol, and ethyl alcohol. Such sensors have no specific selectivity with respect to any one of these substances and so are unable to distinguish in mixtures of reducing gases, as to any single constituent. It has been found that in actual practice where hydrogen sulfide or ammonia are to be quantitatively analyzed by such devices, the ambient atmosphere will contain, as a background, significant quantities of other reducing gases to which the device is sensitive, typically hydrogen in concentrations much higher than the gas to be detected. Inherently, the sensor, which monitors the change in carrier density, does not discriminate between the various reduction reactions which occur.

Thus, the sensor is sensitive to reducible gas concentration in general, but not to any particular reducible gas component. Such a sensor is generally more sensitive to hydrogen than to other reducing gases. The presence in combination of hydrogen or other reducing gas with the hydrogen sulfide or ammonia to be analyzed will produce an erroneous concentration indication for the quantitative analysis. Therefore, for all practical purposes, the device manufactured in accordance with the teaching of the aforesaid patent is not satisfactory for the quantitative analysis of hydrogen sulfide or ammonia.

A variation of the type of detector of U.S. Pat. No. 3,429,257 which is particularly adapted to measure hydrogen sulfide concentration is described in U.S. Pat. No. 3,901,067, issued Aug. 26, 1975. In this patent, a device is described which uses a stannic oxide semiconductor film which is doped with selected metals to provide hydrogen sulfide sensitivity.

SUMMARY OF THE INVENTION

According to the present invention, a quantitative analysis sensor for a reducible gas has a thin tungsten oxide film sensor element with means to provide a specificity of the film for the gas which is to be quantitatively determined. If hydrogen sulfide is to be detected, tungsten trioxide is utilized in the film as the sensitivity controlling component. If ammonia is to be detected, a platinum catalyst is utilized in conjunction with the film.

It has been found that tungsten trioxide exhibits a much greater sensitivity to hydrogen sulfide than to other reducing gases. Other tungsten oxides are not comparably sensitive to hydrogen sulfide. Contrary to the teachings of U.S. Pat No. 3,479,257, and U.S. Pat. No. 3,901,067, the addition of platinum or other such catalytic materials or dopants is not required to produce a sensor sensitive to hydrogen sulfide and the use of such a catalyst or dopant degrades the performance of the hydrogen sulfide sensor of the present invention.

It has been found that the addition of a small amount of platinum catalyst under the tungsten oxide sensor element increases the sensitivity of the tungsten oxide film to ammonia over sensitivity to hydrogen, thus providing an ammonia analyzer. The tungsten oxide film for the sensor element may be formed either by chemical or physical means. By way of example, a chemically formed film may be produced by decomposing a tungsten salt contained in solution and deposited on the sensor, and a physically formed film may be produced by sintering tungsten trioxide, in powdered form, which has been placed on the sensor. If the sensor is to be used to detect ammonia, a platinum catalyst is formed under a tungsten oxide film. The platinum catalyst may similarly be formed chemically by decomposition for example, or physically, by evaporation for example. Thus, in its broadest aspects, the invention contemplates both the method of making such a sensor, the device so made, and the method of detecting the gas.

BRIEF DESCRIPTION OF THE DRAWING

The present invention may be more readily understood by referring to the accompanying drawing, in which.

DESCRIPTION OF THE PREFERRED EMBODIMENTS

Figure 1:
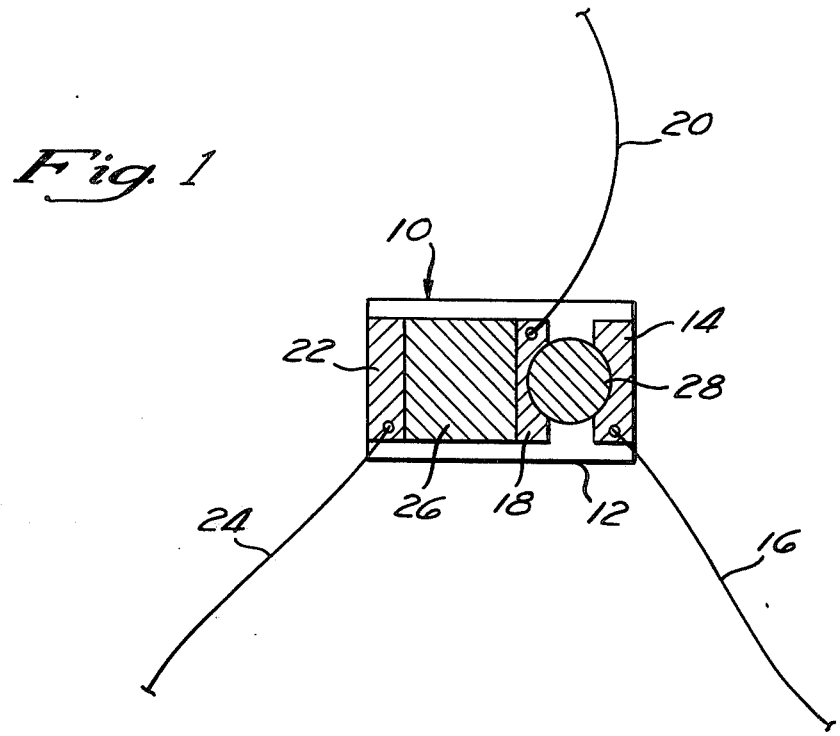
FIG. 1 is a plan view of a sensor according to the present invention.

Referring now to FIG. 1, there is shown a plan view of a sensor 10 according to the present invention. The sensor 10 consists of a base or substrate 12, formed of a nonconducting material. On the substrate 12, there are formed a sensor output terminal 14, having a sensor output lead 16, a ground or common terminal 18 having a ground lead 20, and a heater input terminal 22 having a heater input lead 24. A heater pad 26 is formed between the heater input terminal 22 and the ground terminal 18 on the substrate 12. A thin tungsten oxide film 28, of disc-shaped configuration, is formed on the base 12 so as to extend between the sensor output terminal 14 and the ground terminal 18. If the sensor is to be used to detect ammonia, a platinum catalyst (not shown) has previously been formed on the substrate 12 under the film 28 before the film is deposited on the substrate 12.

With respect to the preferred embodiment shown in FIG. 1, the base or substrate may be formed of type 614 alumina silicate, a product of American Lava Company; the terminals 14, 18, 22 are of gold, the heater pad 26 of EMCA 5000 series resistor ink, a product of Electro Materials Corp. of America, Mamaroneck, New York; and the tungsten oxide film includes tungsten trioxide ($WO_3$). Typical dimensions of such a sensor are as follows: substrate—0.175 inches long, 0.100 inches wide and 0.025 inches thick; heater pad 0.075 inches long and 0.080 inches wide with a resistance of 26 ohms, spacing between ground terminal and sensor output terminal—0.030 inches and the tungsten oxide film of 0.045 inches diameter.

Figure 2:
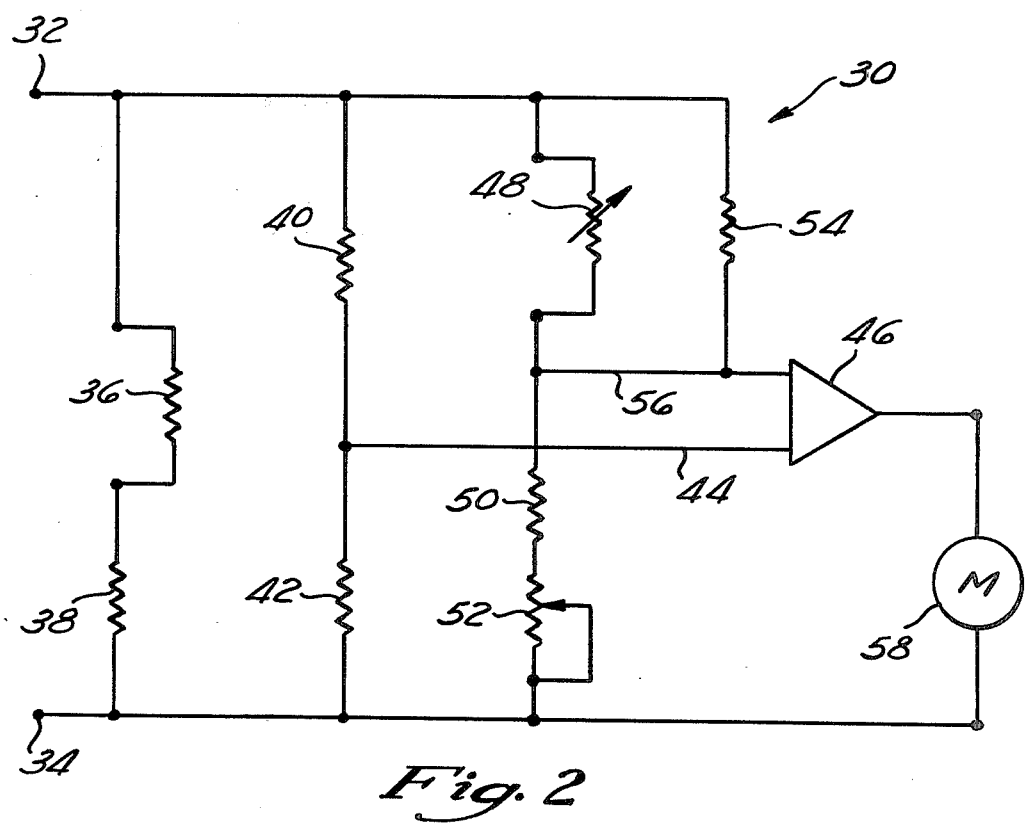
FIG. 2 is a schematic diagram of the electronic circuitry utilized in conjunction with the sensor FIG. 1 to provide for quantitative analysis.

Referring now to FIG. 2, there is shown a sensor circuit 30 for use with the sensor 10 shown in FIG. 1. The sensor circuit 30 has a pair of input terminals 32, 34 across which an actuating potential, typically six volts DC, is applied. The heater pad, shown as a resistance 36, is connected in series with a current limiting resistor 38 across the actuating potential, so as to heat the substrate to a temperature of between 150° and 300° C. The sensor circuit is of the Wheatstone bridge type, and has a pair of matched resistors 40, 42 connected across the actuating potential and connected to a lead 44 to provide a reference potential to am amplifier 46. The resistance of the tungsten oxide film 28 is shown in FIG. 2 as a variable resistor 48 connected in series with a reference resistor 50 and zeroing potentiometer 52 across the actuating potential. Connected in parallel with the variable resistor 48 is a shunt resistor 54 whose resistance approximates the sum of the resistances of the reference resistor 50 and zeroing potentiometer 52. The variable resistor 48, in the absence of the detection of reducible gas, has a resistance in the order of between one and two orders of magnitude greater than the resistance of the shunt resistor 54. Consequently, the shunt resistor 54 and the reference resistor 50 and zeroing potentiometer 52 establish the zero calibration of the sensor. The sensor is calibrated by adjusting the zeroing potentiometer 52 so that the potential applied to the amplifier 46 through a lead 56, the potential between the variable resistor 48 and the reference resistor 50, produces a zero concentration indication on a meter 58 connected between the output of the amplifier 46 and the input terminal 34.

In operation, a reduction reaction occurring at the tungsten oxide film results in a reduction in the resistance of the variable resistor 48, unbalancing the Wheatstone bridge and thereby producing an output reading in the meter 58 which is a function of the concentration of gas being detected. Inasmuch as the sensor of the present invention has a construction preselected to provide a specificity for hydrogen sulfide or ammonia as compared to other reducing gases, the output indication in the meter 58 will provide an indication of the hydrogen sulfide or ammonia content of the gas producing the reduction reaction.

In the preferred embodiment of the hydrogen sulfide sensor the tungsten oxide film consists, either entirely or principally, of tungsten trioxide ($WO_3$). While the thickness of the film is not critical to the invention, a typical film may be of 10,000° A, by way of example. The only limitation of film thickness in the preferred embodiment is that of the structure of the particular sensor. Tungsten trioxide, without a catalyst, provides a specific sensitivity to the hydrogen sulfide reduction reaction sufficient to provide for a usable output signal from the sensor 10. The film may, however, contain other impurities, but, so long as the tungsten trioxide is present in sufficient concentration, the reduction reaction will take place at a sufficient rate to provide the usable output signal. In other words, the concentration of tungsten trioxide in the tungsten oxide film should be sufficient in the preferred embodiment so that the tungsten trioxide controls the specificity of the sensor to provide the required specificity. Such specificity is always obtained when the film consists only of tungsten trioxide and gradually declines, i.e., becomes less specific, as impurities, such as other tungsten oxides, increase in amount in the film.

As tungsten trioxide normally occurs as a powder, it is necessary to provide some method by which the tungsten trioxide can be combined to produce the film 28. In one example of producing the film 28 for the preferred embodiment, tungsten trioxide is mixed with distilled water to provide a suspension. Tungsten trioxide is insoluble in water, and the suspension is preferably as concentrated in tungsten trioxide as is possible. A practical lower limit on the amount of tungsten trioxide which may be contained in the suspension for use in the present invention in the preferred embodiment is a mixture of 10 grams of tungsten trioxide in 640 milliliters of distilled water. The most concentrated suspension which can readily be obtained under normal ambient conditions is a mixture of 10 grams of tungsten trioxide with 80 milliliters of distilled water. The mixture is then further processed by bubbling ammonia through the mixture to produce a solution of ammonium tungstate, $NH_3(WO_4)$. This ammonium tungstate solution is utilized to provide the thin film of pure tungsten trioxide by placing a drop of the ammonium tungstate solution on the sensor base 12 so as to connect the terminals 14, 18. The sensor is then heated to 600° C. for 15 minutes to decompose the ammonium tungstate to produce ammonia, oxygen and tungsten trioxide. Thus, a disc of tungsten trioxide is formed which connects the terminals 14, 18 so as to provide electrical circuit continuity for the sensor. The tungsten trioxide is specifically sensitive to hydrogen sulfide to a much greater degree than to the other reducing gases which may be present, so that the sensor produced is a sensor which has a specificity for hydrogen sulfide.

As an alternative to the forming of the thin tungsten trioxide film 28 by chemical means, such as the just-described decomposition of a salt contained in solution, the film 28 can be formed by physical means. One example of such a physical process is sintering. In this process, tungsten trioxide in its powdered form is deposited on the base 12 of the desired location for the film, i.e., connecting the terminations 14, 18. The sensor is then heated at, for example, from 600° to 1500° C. for from fifteen minutes to twenty-four hours, then by producing a unitary film 18 of tungsten trioxide. Alternatively, the saturated suspension of tungsten trioxide utilized in the chemical decomposition process described above can be utilized. A drop of the suspension is deposited on the base 12, and the base heated as described with respect to sintering the plain powder in order to produce the sintered tungsten trioxide film.

The foregoing description of the preferred embodiment of the hydrogen sulfide sensor utilizes, in the tungsten oxide semiconductor film, a single compound, tungsten trioxide. Obviously, the tungsten oxide film may be varied in its composition by utilization of tungsten dioxide, or other tungsten oxides, or other non-sensitive materials so as to reduce the dominance of the tungsten trioxide as controlling the sensitivity to hydrogen sulfide, while still providing a sufficient concentration of tungsten trioxide to provide hydrogen sulfide specificity. Furthermore, the foregoing description as to the method of making the tungsten oxide film is given by way of example only, as other methods for producing the tungsten oxide film will be readily apparent to those skilled in the art. Therefore, the invention, in its broadest form, comprehends not only the structure produced by the method recited above, but also the method of making a sensor which consists of forming a thin tungsten oxide film between terminals of the sensor so as to provide electrical circuit continuity, in which the tungsten oxide film consists, in its entirety or in part, of tungsten trioxide so that the tungsten trioxide provides the specificity of the sensor to hydrogen sulfide.

Figure 3:
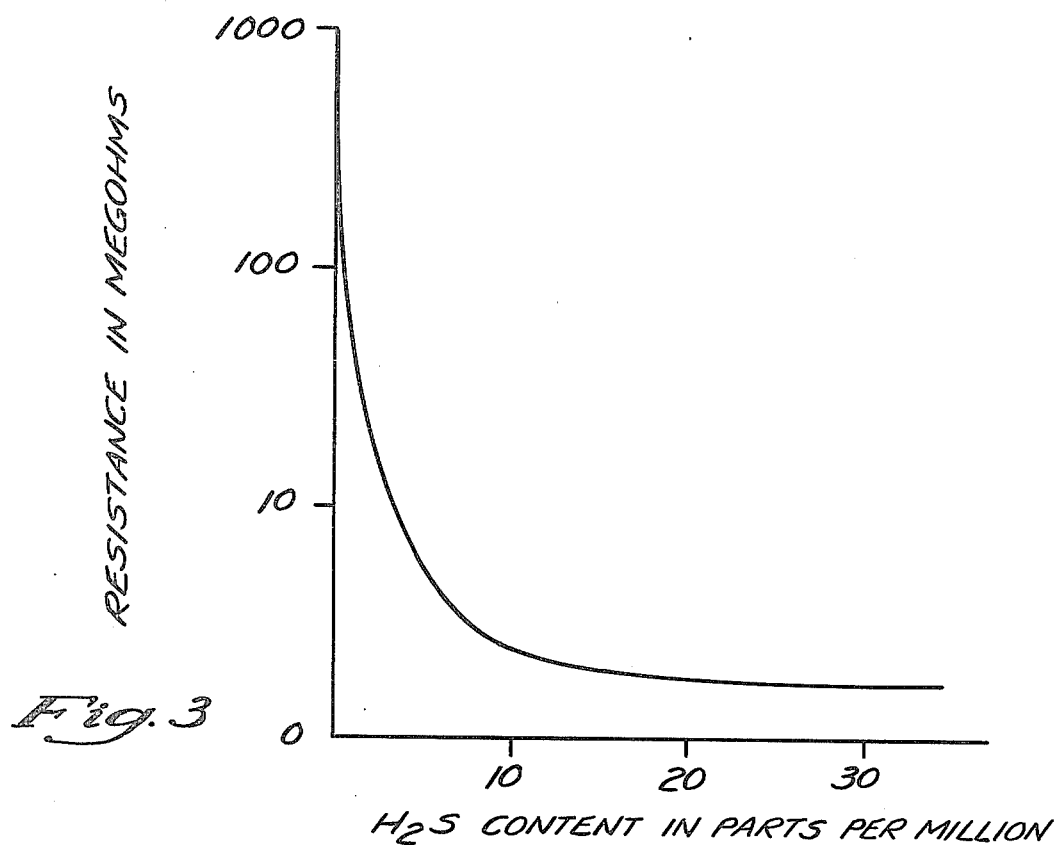
FIG. 3 is a graphical representation of a typical sensor response characteristic of the hydrogen sulfide embodiment of the invention.

Referring now to FIG. 3, there is shown, in graphical representation, the change in resistance with hydrogen sulfide concentration of the preferred embodiment sensor 10 constructed in accordance with FIGS. 1 and 2. As will be seen from FIG. 3, the resistance change rate is nonlinear, decreasing with the increasing concentration of hydrogen sulfide. In a typical sensor constructed according to the invention, the resistance across the tungsten oxide film, that is, the resistance of the variable resistor 48, may vary from as much as three hundred megohms for zero reducible gas concentration to two and one-half megohms for a gas concentration of ten parts per million of hydrogen sulfide.

Figure 4:
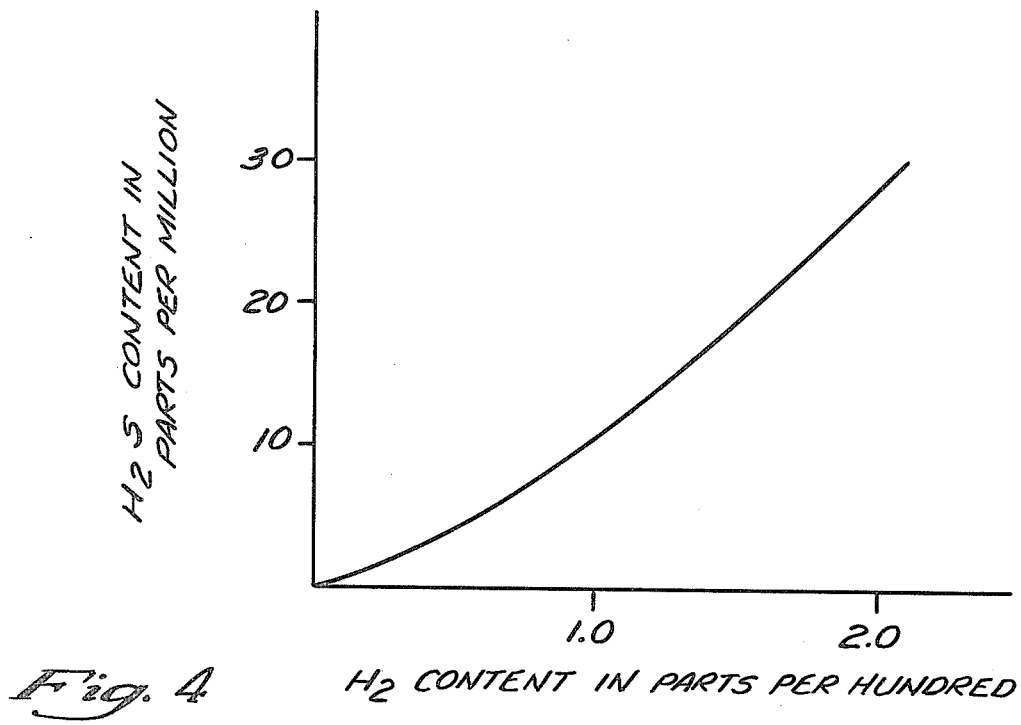
FIG. 4 is a graphical representation of specificity of the hydrogen sulfide embodiment sensor to hydrogen sulfide as compared to hydrogen.

FIG. 4 is a graphical representation of the comparative specificity of the preferred embodiment sensor of the present invention to hydrogen sulfide and hydrogen. Typically, as is shown in FIG. 4, the sensor according to the present invention is at least one thousand times as sensitive to hydrogen sulfide as to hydrogen. Thus, in a typical sensor, a hydrogen sulfide content in the reducible gas of ten parts per million will produce the same sensor output as is produced by a hydrogen concentration of ten thousand parts per million. The specificity of the sensor to hydrogen sulfide reduces with respect to increasing concentrations, so that from the approximately one thousand to one specificity at a hydrogen concentration of one percent, the specificity reduces, at a concentration of two percent, to slightly less than eight hundred to one.

The specificity of the sensor of the present invention for hydrogen sulfide with respect to gases other than hydrogen is generally similar. For example, using a sensor according to the present invention at a concentration of hydrogen sulfide of fifty parts per million, the sensor shows a change in concentration indication of less than one part per million when the sulfur dioxide content of the atmosphere being analyzed changes in concentration from zero to two hundred parts per million. For carbon dioxide, the sensor shows a variation of less than two parts per million in concentration indication for a change in carbon dioxide concentration from zero to one thousand parts per million. For benzene, the sensor shows a similar lack of variation in output concentration indication.

The hydrogen sulfide sensor of the present invention has various applications. The human sense of smell is extremely sensitive to hydrogen sulfide, and in fact a human being cannot, by the sense of smell, detect any increase in concentration of hydrogen sulfide above 0.03 parts per million. In fact, the human sense of smell indicates a decreasing hydrogen sulfide concentration when the concentration increases in the range of from fifty to one hundred parts per million, and does not detect the presence of hydrogen sulfide at all in concentrations greater than one hundred parts per million. Current safety regulations permit work in atmospheres containing not in excess of ten parts per million of hydrogen sulfide without the use of gas masks. With the use of gas masks, in oil drilling platform rigs for example, work may be conducted up to gas concentrations of twenty-five parts per million. Commerical gas use for heating and the like is required by regulation to have a hydrogen sulfide content below 8 parts per million. Consequently, the sensor of the present invention has specific application both as to monitoring atmosphere as to safe working conditions and as to monitoring commercial gas with respect to the permissible maximum hydrogen sulfide content.

In the ammonia specific embodiment of the present invention, prior to forming the tungsten oxide film on the substrate 12, a platinum catalyst is deposited on the substrate so that the tungsten oxide film will overlie the platinum. The platinum may be deposited either physically or chemically so as to form a platinum layer of from fifty to seventy angstroms in thickness. In physical deposition, the amount of platinum deposited as the catalyst is that quantity of platinum which is evaporated in a period of ten seconds into the substrate 12 from a 4 mil platinum wire heated to a temperature of 1000° C. and positioned 0.062 inches from the surface of the base. In chemical deposition, fifty microliters of a one thousand parts per million solution of dihydrogen hexachloroplatinate, $H_2PtCl_6$, is deposited on the substrate and the substrate heated to decompose the solution, leaving a platinum deposit. After the platinum catalyst has been formed on the substrate 12, the tungsten oxide film is formed overlying the platinum. The tungsten oxide layer may be formed in the same manner as previously described with respect to the hydrogen sulfide specific embodiment. In such an embodiment, the platinum catalyst will overcome the dominance of the tungsten trioxide and provide specificity for ammonia rather than by hydrogen sulfide. However, it is not essential that the trioxide of tungsten be used in the ammonia specific embodiments. The platinum catalyst will provide ammonia specificity with other oxides of tungsten, such as tungsten dioxides or mixtures of tungsten oxides. The tungsten oxide film can be formed by vacuum deposition or "sputtering", a process well known in the art.

Figure 5:
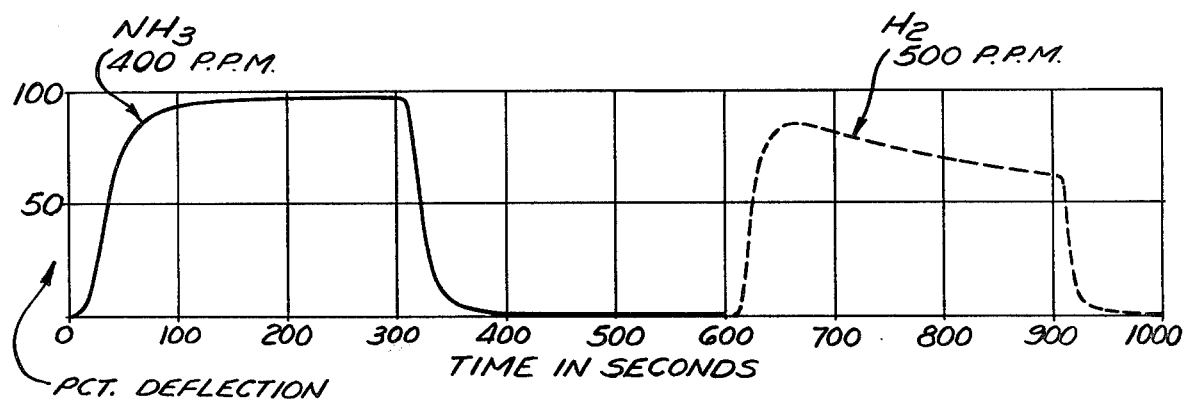
FIG. 5 is a graphical representation of the relative response of an ammonia sensor according to the invention to ammonia and hydrogen.

Referring now to FIG. 5, there is shown a graphical representation of a typical ammonia sensor circuit as illustrated in FIG. 2. As seen in FIG. 5, the ammonia sensor of the present invention shows a more than twenty percent greater output signal for a given concentration of ammonia than for the same concentration of hydrogen. Also, the ammonia sensor of the present invention is comparatively insensitive to hydrogen sulfide.

With respect to the embodiments described above, various dimensional characteristics have been set out. As will be apparent, these dimensional characteristics may be varied without departing from the scope of the present invention.

The invention claimed is:

1. A method of monitoring the hydrogen sulfide content of a gaseous atmosphere which comprises the steps of exposing to said atmosphere a thin film semiconductor coated on an inert refractory substrate, said film being comprised of tungsten trioxide, without a dopant to provide hydrogen sulfide specificity, and diminishing in resistivity with increasing atmospheric concentration of hydrogen sulfide when placed at from about 150° C. to about 300° C. in an air atmosphere containing at least hydrogen sulfide, monitoring the conductivity of said film, and generating a signal proportional to the conductivity of said film so monitored.

2. A method of detecting hydrogen sulfide in a gaseous atmosphere comprising:
heating a thin film of tungsten trioxide between about 150° C. and about 300° C.,
exposing the tungsten trioxide film to the gaseous atmosphere to be monitored,
detecting any change in electrical conductivity of the tungsten trioxide film when so exposed, and
generating a signal proportional to the change in conductivity,
said method characterized in the exclusion from said tungsten trioxide film of a dopant to provide hydrogen sulfide sensitivity.

3. A method of monitoring the ammonia content of gaseous atmosphere which comprises the steps of exposing to said atmosphere a thin film semiconductor coated on an inert refractory substrate, said film having been deposited over a layer of platinum of a thickness of from about fifty to seventy Angstroms formed on the substrate and being principally comprised of a tungsten trioxide and diminishing in resistivity with increasing atmospheric concentration of ammonia when placed at from about 150° C. to about 300° C. in an air atmosphere containing at least ammonia, monitoring the conductivity of said film, and generating a signal proportional to the conductivity of said film so monitored.

4. In a gas sensor, a semiconductive element connected between a pair of sensor output terminals and containing tungsten trioxide in a concentration sufficient to provide a specificity in sensitivity for hydrogen sulfide with respect to other gases which has been deposited over a layer of platinum present in a concentration sufficient to provide a specificity of said element for ammonia with respect to hydrogen sulfide.

5. A sensor having a specificity in sensitivity for ammonia with respect to other reducing gases comprising:
a base of nonconducting material;
a layer of platinum catalyst deposited on said base;
a reducing film formed on said base over the platinum catalyst and containing tungsten oxide as its principal constituent;
means for heating said film to a temperature at which the catalytic reduction of ammonia occurs;
means for measuring changes in resistance in said film in response to reduction reactions occurring at the film surface;
and in which the platinum is deposited on the base in a thickness of from about fifty to about seventy Angstroms.

6. A sensor having a specificity in sensitivity for ammonia with respect to other reducing gases comprising:
a base of a nonconducting material over a portion of which a layer of platinum of from about fifty to about seventy Angstroms in thickness has been deposited;
a reducing film formed over the platinum layer deposited on said base, said film being comprised at least in part of tungsten trioxide in a concentration sufficient, absent said platinum, to provide a film with hydrogen sulfide specificity with respect to ammonia;
means for heating said film to a temperature at which the catalytic reduction of ammonia occurs; and
means for measuring changes in resistance in said film in response to reduction reactions occurring at the film surface.

* * * * *